(12) United States Patent  
Mitamura (10) Patent No.: US 11,839,774 B2
(45) Date of Patent: Dec. 12, 2023

(54) PHOTOTHERAPY ASSISTANCE DEVICE, PHOTOTHERAPY SYSTEM, AND PHOTOTHERAPY ASSISTANCE METHOD

(71) Applicant: OLYMPUS CORPORATION, Tokyo (JP)

(72) Inventor: Motohiro Mitamura, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 17/142,445

(22) Filed: Jan. 6, 2021

(65) Prior Publication Data

US 2021/0146153 A1 May 20, 2021

Related U.S. Application Data

(63) Continuation of application No. PCT/JP2018/025955, filed on Jul. 10, 2018.

(51) Int. Cl.
*A61N 5/06* (2006.01)
*A61M 25/10* (2013.01)

(52) U.S. Cl.
CPC .......... *A61N 5/0603* (2013.01); *A61M 25/10* (2013.01); *A61N 2005/061* (2013.01); *A61N 2005/0632* (2013.01)

(58) Field of Classification Search
CPC .......... A61N 5/0603; A61N 2005/061; A61N 2005/0632; A61M 25/10
See application file for complete search history.

(56) References Cited

U.S. PATENT DOCUMENTS

| | | |
|---|---|---|
| 4,612,938 A | 9/1986 | Dietrich et al. |
| 5,153,900 A | 10/1992 | Nomikos et al. |
| 5,369,679 A | 11/1994 | Sliski et al. |
| 5,422,926 A | 6/1995 | Smith et al. |
| 5,428,658 A | 6/1995 | Oettinger et al. |

(Continued)

FOREIGN PATENT DOCUMENTS

| | | |
|---|---|---|
| EP | 2 548 616 A1 | 1/2013 |
| GB | 2130092 A1 | 5/1984 |

(Continued)

OTHER PUBLICATIONS

Japanese Office Action dated Nov. 2, 2020 received in 2020-529868.

(Continued)

*Primary Examiner* — Allen Porter
*Assistant Examiner* — Skylar Lindsey Christianson
(74) *Attorney, Agent, or Firm* — Scully, Scott, Murphy & Presser, P.C.

(57) ABSTRACT

A phototherapy assistance device includes: a connector that is connectable to a balloon detection unit that detects inflation information regarding whether a balloon has been inflated in a body cavity; and one or more processors including hardware, the one or more processors being configured to: detect connection information regarding whether an optical probe to be inserted into the balloon is connected to a light source device; determine whether the optical probe can be inserted on a basis of the inflation information received from the balloon detection unit via the connector, and the connection information; and report a determined determination result.

10 Claims, 8 Drawing Sheets

(56) References Cited

U.S. PATENT DOCUMENTS

| | | | |
|---|---|---|---|
| 5,442,678 A | 8/1995 | Dinsmore et al. | |
| 5,452,720 A | 9/1995 | Smith et al. | |
| 5,528,652 A | 6/1996 | Smith et al. | |
| 5,621,780 A | 4/1997 | Smith et al. | |
| 5,766,234 A | 6/1998 | Chen et al. | |
| 5,800,478 A | 9/1998 | Chen et al. | |
| 6,491,618 B1 | 12/2002 | Ganz | |
| 2001/0049464 A1 | 12/2001 | Ganz | |
| 2003/0191459 A1 | 10/2003 | Ganz et al. | |
| 2005/0124843 A1 | 6/2005 | Singh | |
| 2006/0004286 A1* | 1/2006 | Chang | A61B 90/16 606/198 |
| 2007/0078500 A1 | 4/2007 | Ryan et al. | |
| 2007/0219600 A1* | 9/2007 | Gertner | A61N 5/0603 607/88 |
| 2007/0270717 A1 | 11/2007 | Tang et al. | |
| 2009/0175576 A1 | 7/2009 | Tang | |
| 2009/0187108 A1 | 7/2009 | Tang et al. | |
| 2009/0227993 A1 | 9/2009 | Tang | |
| 2010/0049182 A1 | 2/2010 | Ryan et al. | |
| 2010/0094109 A1 | 4/2010 | Tang | |
| 2010/0174196 A1 | 7/2010 | Ryan et al. | |
| 2010/0286531 A1 | 11/2010 | Ryan et al. | |
| 2010/0292537 A1 | 11/2010 | Ashida et al. | |
| 2010/0298895 A1* | 11/2010 | Ghaffari | A61B 5/14546 607/116 |
| 2011/0015528 A1 | 1/2011 | Kobayashi | |
| 2012/0078121 A1 | 3/2012 | Ryan et al. | |
| 2012/0330166 A1 | 12/2012 | Tang | |
| 2013/0123642 A1 | 5/2013 | Yamaguchi et al. | |
| 2014/0058271 A1 | 2/2014 | Ryan et al. | |

FOREIGN PATENT DOCUMENTS

| | | | |
|---|---|---|---|
| JP | S59-095065 A | 5/1984 | |
| JP | H09-507913 A | 8/1997 | |
| JP | H11-507284 A | 6/1999 | |
| JP | 2002-017747 A | 1/2002 | |
| JP | 2003-530139 A | 10/2003 | |
| JP | 2010-264061 A | 11/2010 | |
| JP | 2011-019706 A | 2/2011 | |
| JP | 2011-087855 A | 5/2011 | |
| WO | 96/02059 A1 | 1/1996 | |
| WO | 97/32520 A1 | 9/1997 | |
| WO | 2000/78393 A1 | 12/2000 | |
| WO | WO-2005049127 A1 * | 6/2005 | A61M 25/1011 |
| WO | 2011/114653 A1 | 9/2011 | |

OTHER PUBLICATIONS

International Search Report dated Oct. 9, 2018 issued in International Application No. PCT/JP2018/025955, together with partial English translation.

* cited by examiner

PHOTOTHERAPY ASSISTANCE DEVICE, PHOTOTHERAPY SYSTEM, AND PHOTOTHERAPY ASSISTANCE METHOD

CROSS-REFERENCE TO RELATED APPLICATIONS

This is a continuation of International Application PCT/JP2018/025955, with an international filing date of Jul. 10, 2018, which is hereby incorporated by reference herein in its entirety.

TECHNICAL FIELD

The present invention relates to a phototherapy assistance device, a phototherapy system, and a phototherapy assistance method.

BACKGROUND ART

A therapeutic method that involves treating bladder cancer by radiating light from a light-emitting probe inserted into a balloon while the bladder is being pressed and expanded by the balloon inflated inside the bladder is known (for example, see PTL 1).

CITATION LIST

Patent Literature

{PTL 1} United States Patent Application Publication No. 2005/124843

SUMMARY OF INVENTION

An aspect of the present invention is directed to a phototherapy assistance device comprising: a connector that is connectable to a balloon detection unit that detects inflation information regarding whether a balloon has been inflated in a body cavity; and one or more processors comprising hardware, the one or more processors being configured to: detect connection information regarding whether an optical probe to be inserted into the balloon is connected to a light source device; determine whether the optical probe can be inserted on a basis of the inflation information received from the balloon detection unit via the connector, and the connection information; and report a determined determination result.

Another aspect of the present invention is directed to a phototherapy assistance method including: detecting inflation information indicating whether a balloon has been inflated in a body cavity; detecting connection information indicating whether an optical probe to be inserted into the balloon is connected to a light source device; determining whether the optical probe can be inserted on a basis of the detected inflation information and connection information; and reporting a determination result.

Another aspect of the present invention is directed to a phototherapy assistance system comprising: a catheter having a distal end equipped with a balloon; an injector that is connected to a proximal end of the catheter and supplies gas to the balloon via the catheter; a valve that is provided on the catheter and opens and closes a supply channel of the gas; an open/close sensor that detects an open/close state of the valve; an optical probe to be inserted into the balloon from a proximal end side of the catheter; a phototherapy assistance device that includes: a probe connector for connecting the optical probe to a light source device, and a wire connector for forming connection to an output wire of the open/close sensor, wherein the phototherapy assistance device detects whether the balloon has been inflated in a body cavity on a basis of an output signal from the open/close sensor, detects whether the optical probe is connected to the light source device, and determines whether the optical probe can be inserted on a basis of both detection results.

DESCRIPTION OF EMBODIMENTS

A phototherapy assistance device 3, a phototherapy system 1, and a phototherapy assistance method according to one embodiment of the present invention will now be described with reference to the drawings.

Figure 1:
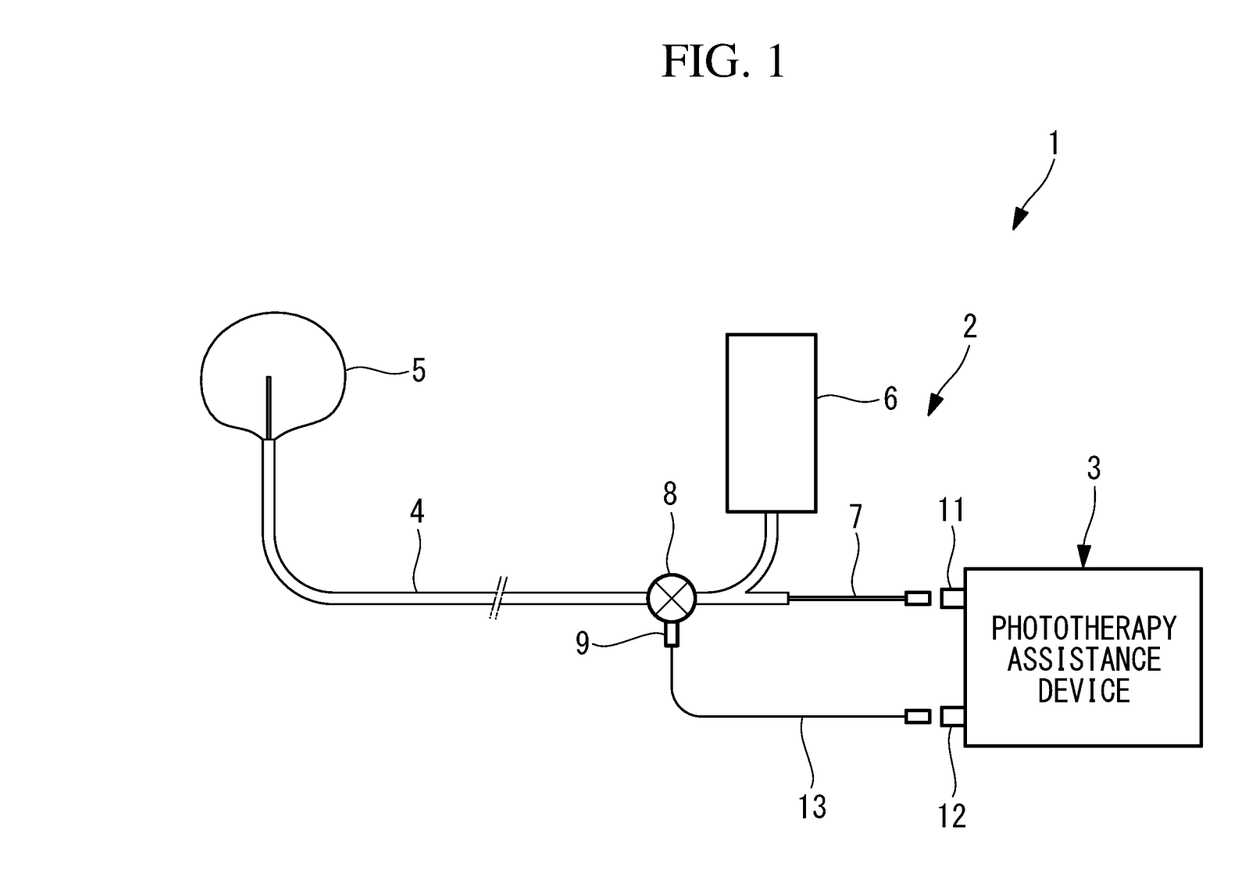
FIG. 1 is an overall structural diagram illustrating a phototherapy system according to one embodiment of the present invention.

As illustrated in FIG. 1, the phototherapy system 1 of this embodiment is equipped with a phototherapy device 2 and a phototherapy assistance device 3.

The phototherapy device 2 is equipped with a long and thin flexible catheter 4 to be inserted into a body cavity, for example, the bladder, via a lumen, for example, the ureter; a balloon 5 that is disposed at a distal end of the catheter 4 and can transmit light; an injector 6 that is connected to a proximal end of the catheter 4 and is used for injecting, into the catheter 4, gas to be supplied to the balloon 5 via the catheter 4; an optical probe (light-emitting probe) 7 that is inserted into the catheter 4 from the proximal end side and emits therapeutic light from a distal end thereof disposed inside the balloon 5 inflated at the distal end of the catheter 4.

The catheter 4 is equipped with a valve 8 that opens and closes an inner hole for supplying the gas, and an open/close sensor (balloon detection unit) 9 that detects the open/close state of the valve 8. When the valve 8 is opened, gas is supplied into the inside of the balloon 5, which is disposed at the distal end of the catheter 4, via the inner hole of the catheter 4 from the injector 6, and the balloon 5 is inflated as a result.

Figure 2:
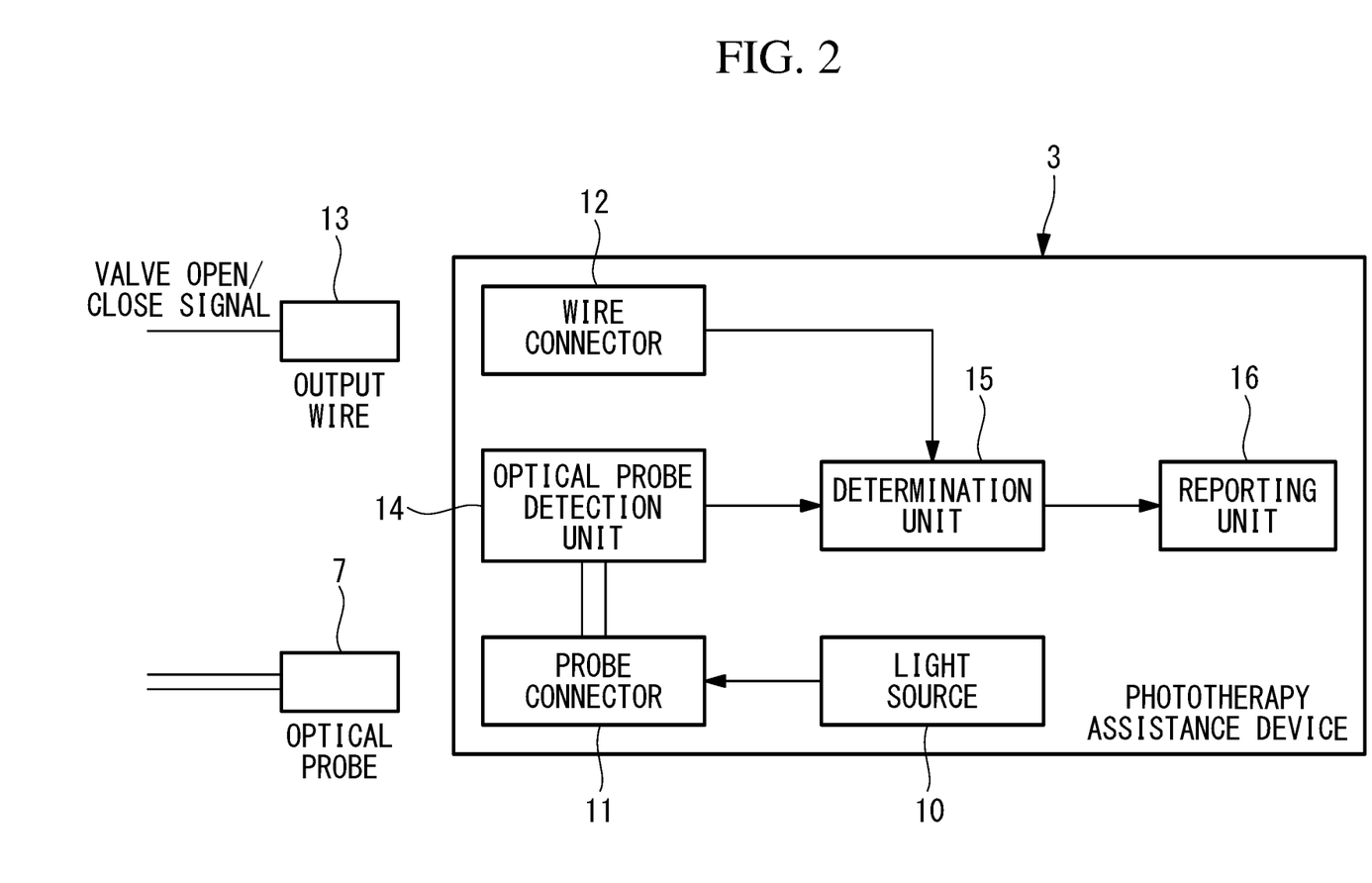
FIG. 2 is a block diagram illustrating a phototherapy assistance device illustrated in FIG. 1.

As illustrated in FIGS. 1 and 2, the phototherapy assistance device 3 of this embodiment is equipped with a light source (light source device) 10 that emits light, for example, infrared light, that irradiates an affected area, a probe connector 11 that connects an optical probe 7 to the light source 10, and a wire connector 12 that connects to an output wire 13 of the open/close sensor 9.

Furthermore, the phototherapy assistance device 3 is also equipped with an optical probe detection unit 14 that detects whether the optical probe 7 is connected to the probe connector 11, a determination unit 15 that makes a determination on the basis of a detection signal from the optical probe detection unit 14 and an valve 8 open/close signal sent via the output wire 13 connected to the wire connector 12, and a reporting unit 16 that reports the determination result.

Figure 3:
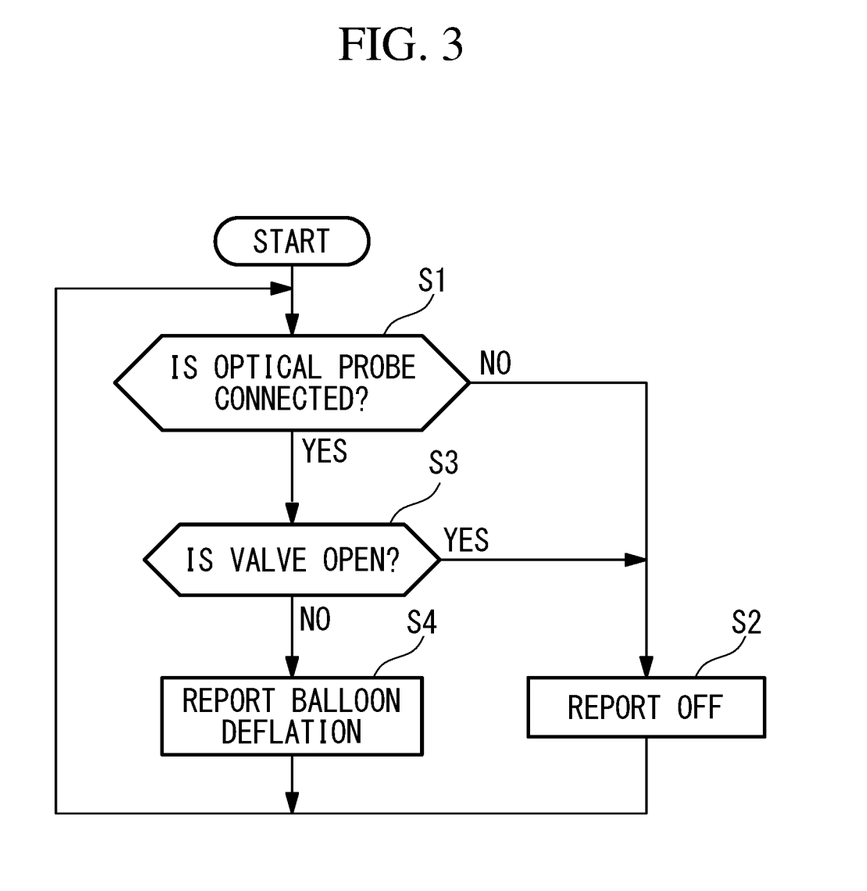
FIG. 3 is a flowchart illustrating the operation of the phototherapy assistance device illustrated in FIG. 1.

As illustrated in FIG. 3, the determination unit 15 determines, through the optical probe detection unit 14, whether the optical probe 7 is connected to the probe connector 11 (step S1), and, if NO, the report from the reporting unit 16 is set to OFF (step S2). When the connection of the optical probe 7 to the probe connector 11 is detected in step S1, the determination unit 15 determines whether the valve 8 is open on the basis of a detection signal from the open/close sensor 9 (step S3). When the valve 8 is open, the determination unit 15 determines that the balloon 5 has been inflated and sets the report from the reporting unit 16 to OFF (step S2). When the valve 8 is not open, the determination unit 15 determines that the balloon 5 has been deflated and reports this determination through the reporting unit 16 (step S4).

A phototherapy assistance method that uses the phototherapy assistance device 3 of this embodiment having the aforementioned features will now be described. The phototherapy assistance method of this embodiment includes detecting inflation information regarding whether the balloon 5 has been inflated in a body cavity, detecting connection information regarding whether the optical probe 7 to be inserted into the balloon 5 is connected to the light source 10, determining whether the optical probe 7 can be inserted on the basis of the detected inflation information and connection information, and reporting the determination result.

In a state in which the optical probe 7 is not connected to the probe connector 11, the report from the reporting unit 16 is set to OFF. The operator inserts the catheter 4 into the lumen until the distal end of the catheter 4 is inside the body cavity. In this state, when the operator connects the optical probe 7 to the probe connector 11, the determination unit 15 determines that the optical probe 7 is connected and examines the detection signal from the open/close sensor 9.

When the valve 8 is not detected to be open, the reporting unit 16 reports that the balloon 5 is in a deflated state, and this prevents the operator from inserting the optical probe 7. When the valve 8 is detected to be open, the report from the reporting unit 16 is set to OFF, and thus the operator can start inserting the optical probe 7 into the catheter 4.

In other words, damage to the balloon 5 and interference of the distal end of the optical probe 7 against the body cavity inner wall caused by insertion of the optical probe 7 into a deflated balloon 5 can be prevented. In addition, it becomes possible to perform phototherapy on the affected area by irradiating the affected area with infrared light emitted from the distal end of the optical probe 7 disposed inside the balloon 5 that is in an inflated state in the body cavity. In other words, the phototherapy assistance device 3 of this embodiment offers an advantage in that phototherapy can be appropriately assisted by providing the operator with the information regarding whether it is recommendable to insert optical probe 7.

In this embodiment, the optical probe 7 may be equipped with an insertion amount sensor (insertion amount detection unit) (not illustrated in the drawings), such as a linear scale, that detects the amount to be inserted into the catheter 4.

Figure 4:
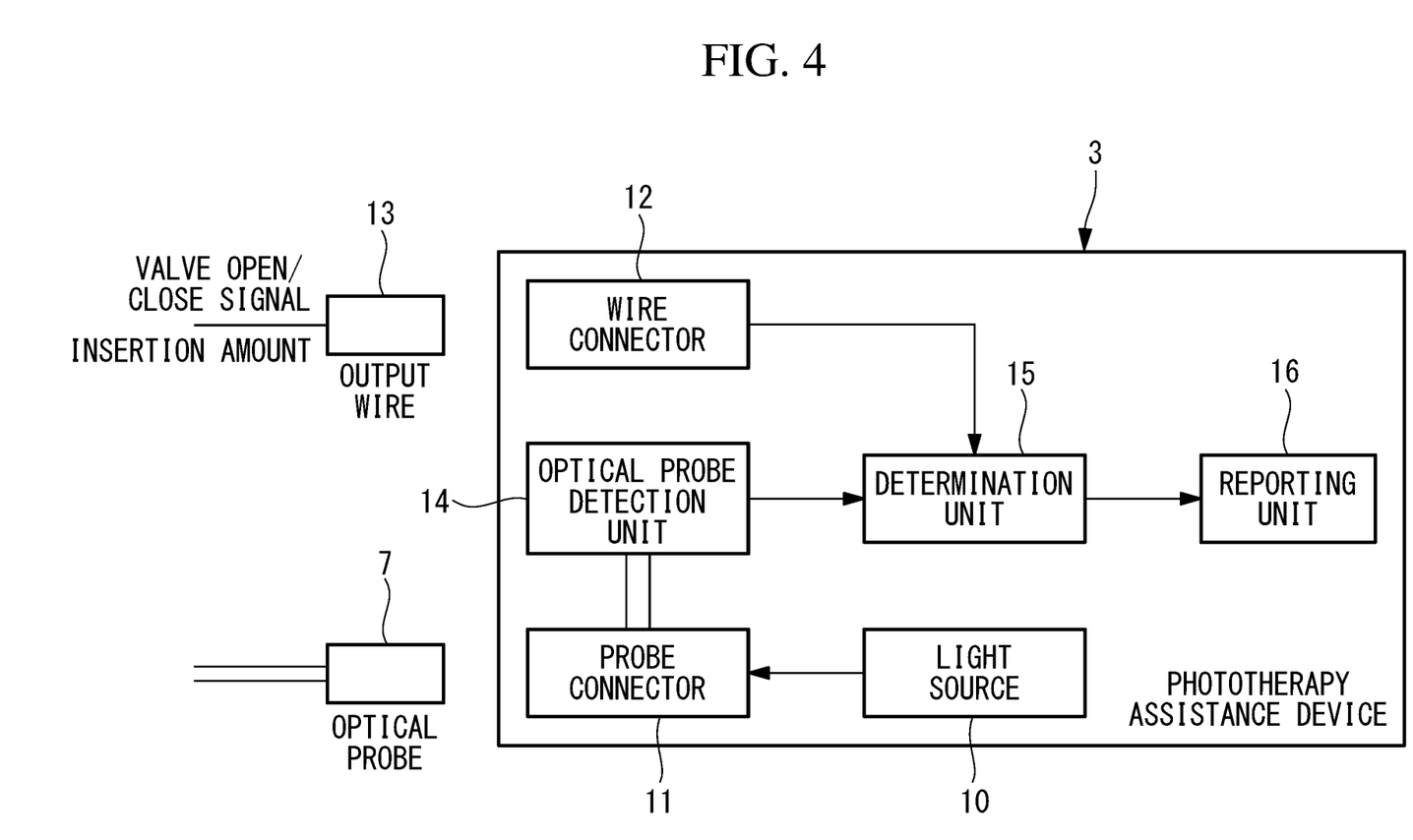
FIG. 4 is a block diagram illustrating a modification of the phototherapy assistance device illustrated in FIG. 2.

In this case, as illustrated in FIG. 4, an output wire of the insertion amount sensor is connected to the wire connector 12, in addition to the output wire 13 of the open/close sensor 9. The determination unit 15 determines whether the insertion amount detected with the insertion amount sensor is within an appropriate range, and, when the amount has reached the appropriate range, the determination unit 15 outputs this determination to the reporting unit 16; subsequently, the reporting unit 16 provides a report to this effect.

Figure 5:
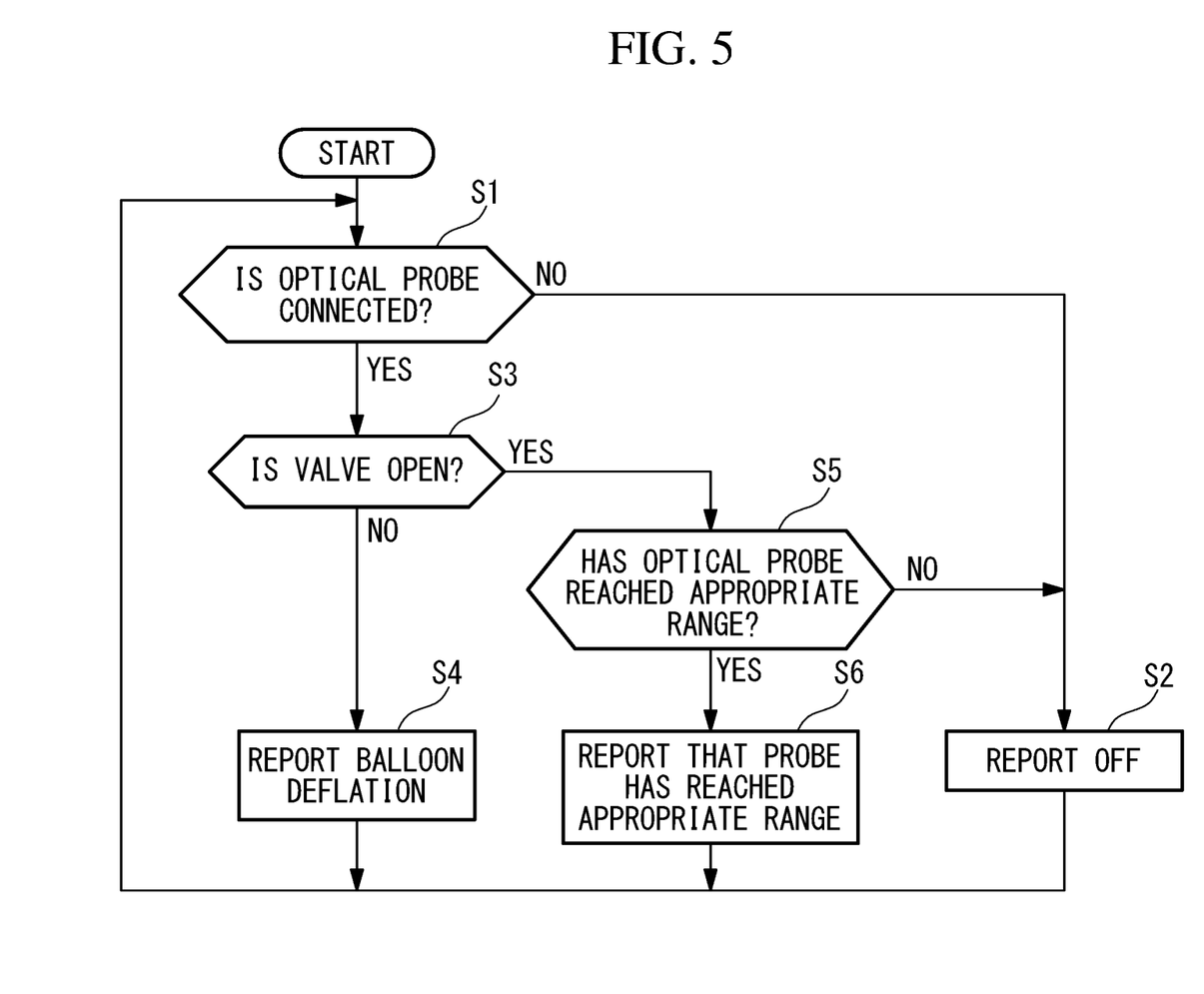
FIG. 5 is a flowchart illustrating the operation of the phototherapy assistance device illustrated in FIG. 4.

In other words, as illustrated in FIG. 5, when the valve 8 is detected to be open in step S3, the determination unit 15 determines whether the optical probe 7 has reached the appropriate range (step S5). When the optical probe 7 has reached the appropriate range, this determination is reported (step S6), and when not, the report is set to OFF (step S2).

In this manner, the operator can easily recognize that the distal end of the optical probe 7 has reached an appropriate position in the balloon 5. In a state in which the distal end of the optical probe 7 is placed at an appropriate position inside the balloon 5, the operator can actuate the optical probe 7 to emit light having an intensity necessary for phototherapy, and this provides an advantage in that the phototherapy can be effectively performed.

Figure 6:
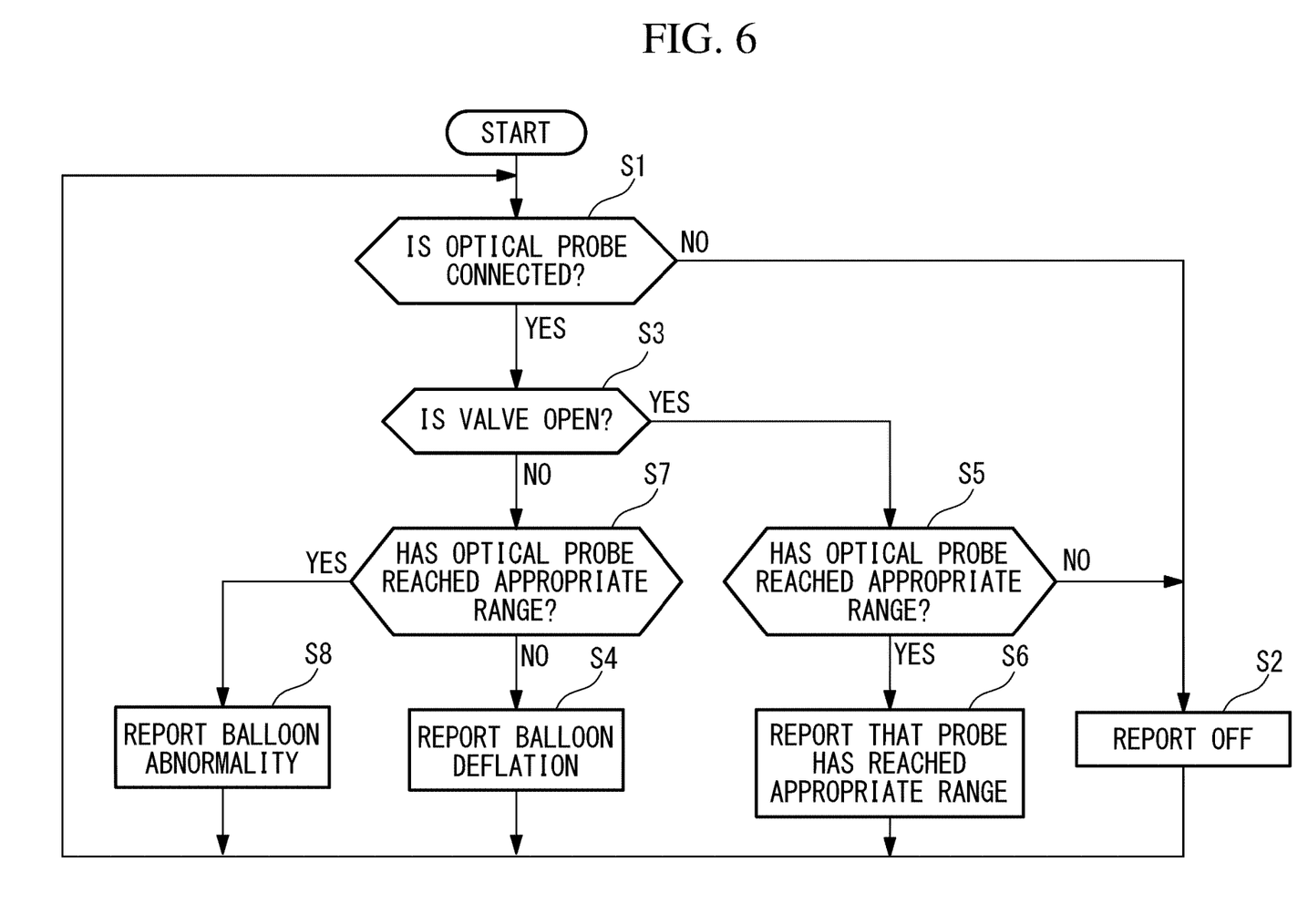
FIG. 6 is a flowchart illustrating a modification of the operation of the phototherapy assistance device illustrated in FIG. 5.

It should be noted that the state of the balloon 5 may be checked again after the reporting unit 16 has reported that the distal end of the optical probe 7 has reached an appropriate position inside the balloon 5. That is, even when the optical probe 7 has reached the appropriate position, the phototherapy cannot be conducted if the balloon 5 has become deflated for some reason. In such a case, as illustrated in FIG. 6, a report indicating deflation of the balloon 5 may be issued (step S4), or, provided that the optical probe 7 has reached the appropriate range (step S7), a report indicating abnormality in the balloon 5 may be issued (step S8).

Figure 7:
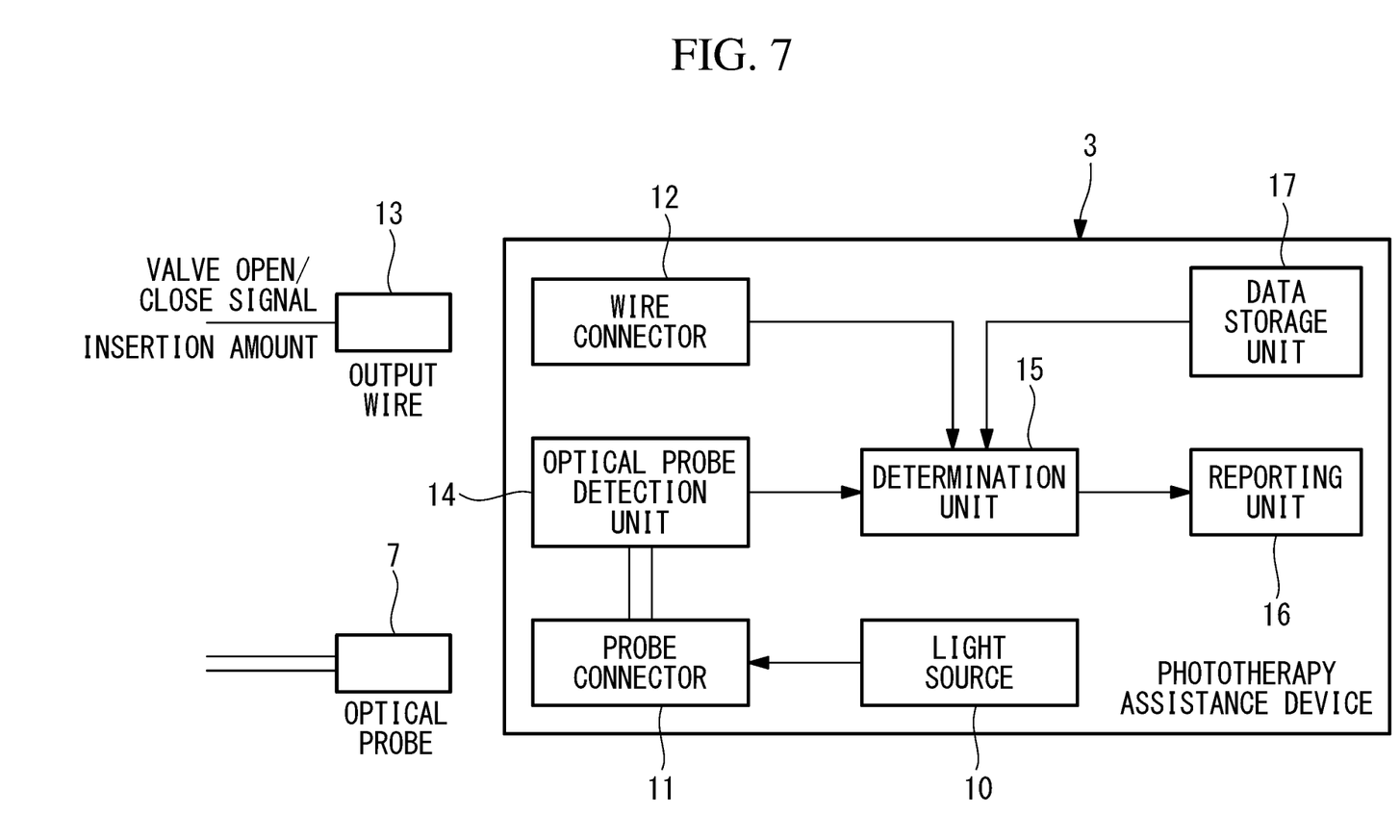
FIG. 7 is a block diagram illustrating another modification of the phototherapy assistance device illustrated in FIG. 2.

In addition, as illustrated in FIG. 7, the phototherapy assistance device 3 may be equipped with a data storage unit (storage unit) 17 that stores an appropriate insertion amount range for the optical probe 7 used in determining whether the optical probe 7 has reached the appropriate range. Here, the determination unit 15 may compare the insertion amount detected with the insertion amount sensor and the appropriate insertion amount range stored in the data storage unit 17 and may determine that the insertion amount is appropriate when the detected insertion amount is within the appropriate insertion amount range. In this case, the appropriate insertion amount range may be set for each patient on the basis of the patient information acquired in advance by CT or the like.

Figure 8:
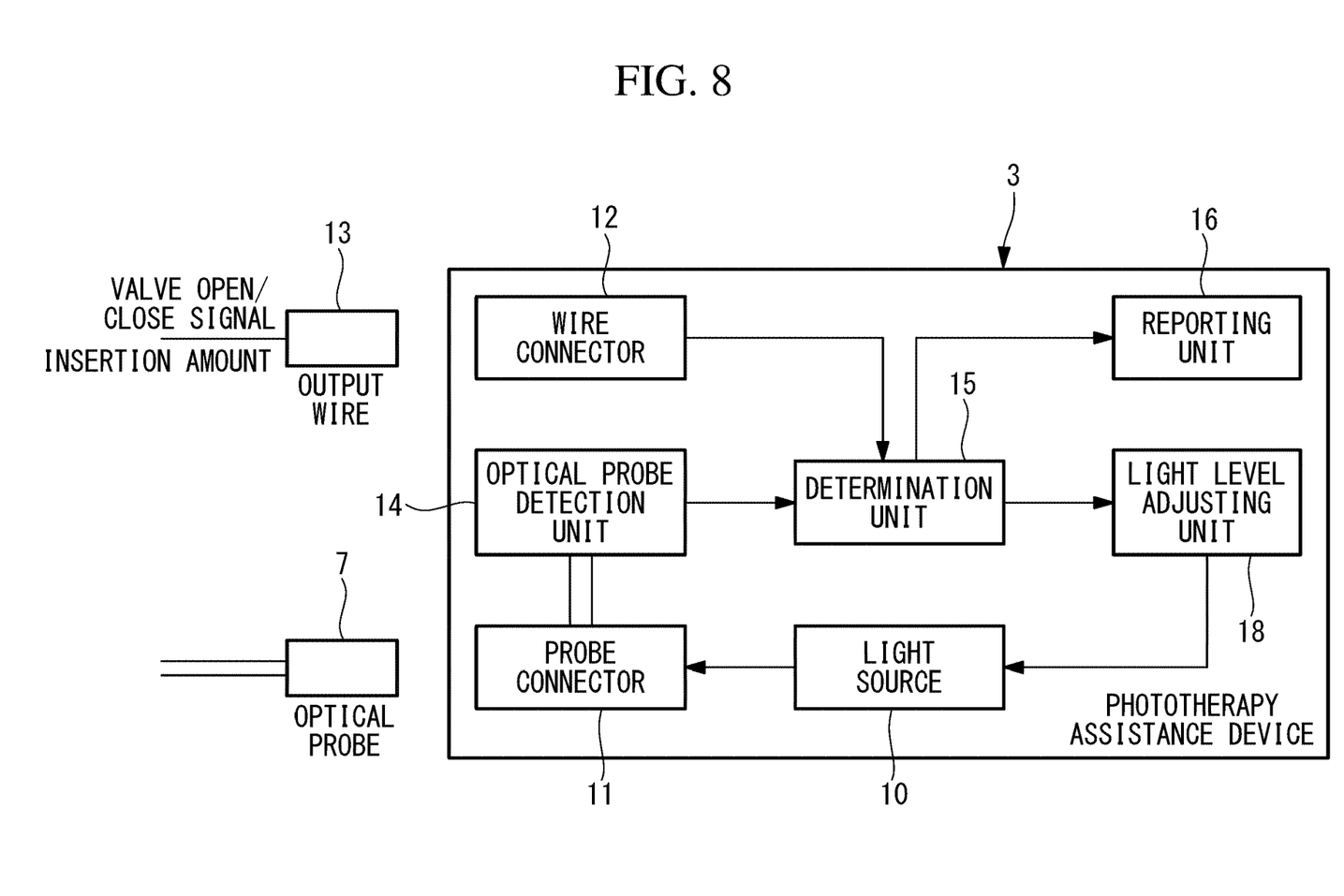
FIG. 8 is a block diagram illustrating another modification of the phototherapy assistance device illustrated in FIG. 2.

Furthermore, as illustrated in FIG. 8, the phototherapy assistance device 3 may be further equipped with a light level adjusting unit (light source control unit) 18 that adjusts the light level of the infrared light emitted from the light source 10 simultaneously with the report indicating that the optical probe 7 has reached the appropriate position while the balloon 5 is in an inflated state and the optical probe 7 is disposed at an appropriate position.

In other words, during the course of inserting the optical probe 7 via the inner hole of the catheter 4, the light level adjusting unit 18 may limit the intensity of the light emitted from the light source 10, and, when it is detected that the balloon 5 has been inflated and the optical probe 7 has reached the appropriate position, this limitation may be cancelled so that light having a light level necessary for phototherapy is emitted from the light source 10.

In this manner, the unintended occurrence of emission of high-intensity light during the course of inserting the optical probe 7 can be prevented. Limiting the light level may involve completely shutting off the light source 10, or limiting the light level to just high enough to make the position of the distal end of the optical probe 7 visually recognizable from outside of the body.

In this embodiment, the open/close sensor 9 that detects the opening/closing of the valve 8 is employed as the balloon detection unit in order to determine whether the balloon 5 has been inflated or deflated; alternatively, the pressure inside the balloon 5 may be detected with a pressure meter and whether the balloon 5 has been inflated may be determined on the basis of the detected pressure.

Moreover, in this embodiment, the report is set to OFF in the reporting unit 16 when the optical probe detection unit 14 detects that the optical probe 7 is not connected to the probe connector 11 and when the valve 8 is open; alternatively, a report indicating that the optical probe 7 is not connected and that the valve 8 is open may be issued.

As a result, the above-described embodiment leads to the following aspects.

An aspect of the present invention is directed to a phototherapy assistance device that includes a balloon detection unit that detects inflation information regarding whether a balloon has been inflated in a body cavity; an optical probe detection unit that detects connection information regarding whether an optical probe to be inserted into the balloon is connected to a light source device; a determination unit that determines whether the optical probe can be inserted on a basis of the detected inflation information and connection information; and a reporting unit that reports a determination result determined by the determination unit.

According to this aspect, when the balloon inserted into the body cavity has been inflated, the balloon detection unit detects inflation information indicating that the balloon has been inflated, and when the balloon has been deflated, the balloon detection unit detects inflation information indicating that the balloon has been deflated. Moreover, the optical probe detection unit detects connection information regarding whether the optical probe inserted into the balloon is connected to the light source device. Then, on the basis of the detected inflation information and connection information, the determination unit determines whether the optical probe can be inserted, and the determination result is reported in the reporting unit. As a result, the operator is provided with the information regarding whether it is recommendable to insert the optical probe, and the phototherapy can be appropriately assisted.

In the aspect described above, the determination unit may determine that the optical probe cannot be inserted when the optical probe detection unit detects the connection information indicating that the optical probe is connected to the light source device and when the balloon detection unit detects the inflation information indicating that the balloon has been deflated, and the determination unit may determine that the optical probe can be inserted when the optical probe detection unit detects the connection information indicating that the optical probe is connected to the light source device and when the balloon detection unit detects the inflation information indicating that the balloon has been inflated.

According to this feature, when the optical probe detection unit detects connection information indicating that the optical probe is connected to the light source device, the determination unit determines that the optical probe can be inserted provided that the balloon detection unit detects inflation of the balloon. Furthermore, when deflation of the balloon is detected, the determination unit determines that the optical probe cannot be inserted. Thus, insertion of the optical probe into the balloon that remains deflated in the body cavity can be prevented, and damage on the balloon by the optical probe can also be prevented.

In the aspect described above, the phototherapy assistance device may be further equipped with an insertion amount detection unit that detects an insertion amount of the optical probe, and when the determination unit determines that the optical probe can be inserted, the determination unit may determine whether the insertion amount detected with the insertion amount detection unit is within an appropriate range.

In this manner, the distal end of the optical probe can be placed at an appropriate position inside the inflated balloon, and the inner wall of the body cavity can be appropriately irradiated with light.

In the aspect described above, the determination unit may determine that there is an abnormality in the balloon when the balloon detection unit detects the inflation information indicating that the balloon has been deflated in a state in which the insertion amount detected with the insertion amount detection unit is within the appropriate range.

According to this feature, even when the insertion amount is within the appropriate range, a report indicating an abnormality in the balloon is issued if the balloon has not been inflated. Thus, phototherapy under abnormal conditions can be avoided, and the phototherapy can be appropriately assisted.

In the aspect described above, the phototherapy assistance device may be further equipped with a storage unit that stores the appropriate range of the insertion amount of the optical probe, and the appropriate range may be set on a basis of CT information of a patient.

According to this feature, whether insertion of the probe is appropriate can be determined for each patient on the basis of the appropriate range of the probe insertion amount determined from the CT information.

In the aspect described above, the phototherapy assistance device may be further equipped with a light source control unit that controls the light source device on a basis of the determination result determined by the determination unit, and the determination unit may determine that light having a light level suitable for phototherapy can be emitted when the insertion amount detected with the insertion amount detection unit is within the appropriate range and when the balloon detection unit detects the inflation information indicating that the balloon has been inflated.

According to this feature, the operator can actuate the optical probe to emit light having a light level suitable for phototherapy on the basis of the reported determination result, and thus can perform appropriate phototherapy on the affected area.

Another aspect of the present invention is directed to a phototherapy system equipped with any one of the phototherapy assistance devices described above, a catheter having a distal end equipped with a balloon, and an optical probe that is to be inserted into the catheter and emits light when inside the balloon.

Another aspect of the present invention is directed to a phototherapy assistance method including: detecting inflation information indicating whether a balloon has been inflated in a body cavity; detecting connection information indicating whether an optical probe to be inserted into the balloon is connected to a light source device; determining whether the optical probe can be inserted on a basis of the detected inflation information and connection information; and reporting a determination result.

The present invention offers the advantageous effect that phototherapy can be appropriately assisted by providing an operator with information regarding whether it is recommendable to insert a light-emitting probe.

REFERENCE SIGNS LIST 1 phototherapy system
3 phototherapy assistance device
4 catheter
5 balloon
7 optical probe
9 open/close sensor (balloon detection unit)
10 light source (light source device)
14 optical probe detection unit
15 determination unit
16 reporting unit
17 data storage unit (storage unit)
18 light level adjusting unit (light source control unit)

The invention claimed is:

1. A phototherapy assistance device comprising:
a first connector connected to or detachably connected to an output wire of an open/close sensor equipped to a valve to supply a gas to a balloon provided at a distal end of a catheter, the open/close sensor being configured to detect an open/close state of the valve and to generate a first signal indicating whether the open/close sensor senses that the balloon has been inflated;
a second connector connected to or detachably connected to an optical probe being inserted into the balloon;
an optical probe detection sensor configured to sense a connected state between the optical probe and a light source that generates therapeutic light, and to generate a second signal indicating that the optical probe to be inserted into the balloon is connected to the light source; and
one or more processors comprising hardware, the one or more processors being configured to:
receive the first signal indicating whether the open/close sensor senses that the balloon has been inflated through the first connector;
receive the second signal indicating whether the optical probe detection sensor senses that the optical probe to be inserted into the balloon is connected to the light source through the second connector; and
in response to receiving the first signal indicating that the open/close sensor senses that the balloon has been inflated and the second signal indicating that the optical probe detection sensor senses that the optical probe to be inserted into the balloon is connected to the light source, generate a third signal indicating that the optical probe that is connected to the light source can be inserted into the balloon that is inflated without one or more of damage to the balloon in a deflated state and interference of the optical probe against a body cavity.

2. The phototherapy assistance device according to claim 1,
wherein the one or more processors are configured to:
in response to receiving both of the first signal indicating that the open/close sensor senses that the balloon has been inflated and the second signal indicating that the optical probe detection sensor senses that the optical probe to be inserted into the balloon is connected to the light source, generate the third signal indicating that the optical probe that is connected to the light source can be inserted into the balloon that is inflated without one or more of damage to the balloon in the deflated state and interference of the optical probe against the body cavity.

3. The phototherapy assistance device according to claim 2,
wherein the one or more processors is configured to:
in response to receiving both of the first signal indicating that the open/close sensor senses that the balloon has not been inflated and the second signal indicating that the optical probe detection sensor senses that the optical probe to be inserted into the balloon is connected to the light source, generate a fourth signal indicating that the optical probe that is connected to the light source cannot be inserted into the balloon that is not inflated.

4. The phototherapy assistance device according to claim 2,
wherein the one or more processors are configured to:
receive a fourth signal from an insertion amount sensor indicating an insertion amount of the optical probe; and
in response to receiving both of the first signal indicating that the open/close sensor senses that the balloon has not been inflated and the second signal indicating that the optical probe detection sensor senses that the optical probe to be inserted into the balloon is connected to the light source, determine, based on the fourth signal, whether the insertion amount of the optical probe is within a predetermined range.

5. The phototherapy assistance device according to claim 4,
wherein the one or more processors are configured to:
in response to determining that the insertion amount of the optical probe is within a predetermined range, generate a fifth signal indicating an abnormality in the balloon.

6. The phototherapy assistance device according to claim 4,
wherein the predetermined range is set on a basis of computerized tomography information of a patient.

7. The phototherapy assistance device according to claim 4,
wherein the one or more processors are configured to:
receive a fourth signal from an insertion amount sensor indicating an insertion amount of the optical probe; and
in response to receiving both of the first signal indicating that the open/close sensor senses that the balloon has been inflated and the second signal indicating that the optical probe detection sensor senses that the optical probe to be inserted into the balloon is connected to the light source,
determine, based on the fourth signal, whether the insertion amount of the optical probe is within a predetermined range; and
in response to determining that the insertion amount of the optical probe is within the predetermined range, generate a fifth signal for controlling the light source to emit light at a level suitable for phototherapy.

8. A phototherapy assistance method performed with a phototherapy assistance device, the phototherapy assistance method comprising:
receiving, by one or more processors comprising hardware of the phototherapy assistance device, a first signal indicating whether an open/close sensor, the open/close sensor being connected to or detachably connected to a first connector of the phototherapy assistance device, senses that a balloon has been inflated, the open/close sensor being equipped to a valve to supply a gas to the balloon provided at a distal end of a catheter;

receiving, by the one or more processors, a second signal indicating whether an optical probe detection sensor senses that an optical probe, the optical probe being connected to or detachably connected to a second connector of the phototherapy assistance device, to be inserted into the balloon is connected to a light source; and in response to receiving the first signal indicating that the open/close sensor senses that the balloon has been inflated and the second signal indicating that the optical probe detection sensor senses that the optical probe to be inserted into the balloon is connected to the light source, generating a third signal indicating that the optical probe that is connected to the light source can be inserted into the balloon that is inflated without one or more of damage to the balloon in a deflated state and interference of the optical probe against a body cavity.

9. A phototherapy assistance system comprising:

a catheter;

a balloon arranged at a distal end of the catheter;

an injector connected to a proximal end of the catheter, the injector being configured to supply gas to the balloon via the catheter;

a valve provided on the catheter, the valve being configured to open and close a supply channel of the gas;

a first connector;

an open/close sensor, an output wire of the open/close sensor being connected to or detachably connected to the first connector, the open/close sensor being configured to detect an open/close state of the valve and to generate a first signal indicating whether the open/close sensor senses that a balloon has been inflated;

a second connector;

an optical probe connected to or detachably connected to the second connector, the optical probe being configured to be inserted into the balloon from a proximal end side of the catheter;

an optical probe detection sensor configured to detect whether the optical probe is connected to a light source and to generate a second signal indicating whether the optical probe detection sensor senses that the optical probe to be inserted into the balloon is connected to the light source; and one or more processors comprising hardware, the one or more processors being configured to in response to the first signal indicating that the open/close sensor senses that the balloon has been inflated and the second signal indicating that the optical probe detection sensor senses that the optical probe to be inserted into the balloon is connected to the light source, generate a third signal indicating that the optical probe that is connected to the light source can be inserted into the balloon that is inflated without one or more of damage to the balloon in a deflated state and interference of the optical probe against a body cavity.

10. The phototherapy assistance system according to claim 9, wherein the one or more processors are configured to, in response to receiving both of the first signal indicating that the open/close sensor senses that the balloon has been inflated and the second signal indicating that the optical probe detection sensor senses that the optical probe to be inserted into the balloon is connected to the light source, generate the third signal indicating that the optical probe that is connected to the light source can be inserted into the balloon that is inflated without one or more of damage to the balloon in the deflated state and interference of the optical probe against the body cavity.

* * * * *